US008642275B2

(12) United States Patent
Przewodowski

(10) Patent No.: US 8,642,275 B2
(45) Date of Patent: Feb. 4, 2014

(54) IMMUNOLOGICAL TESTS FOR THE PRESENCE OF BACTERIA WHICH MAKE USE OF ANTIBODIES OBTAINED USING A SPECIFIC METHOD

(75) Inventor: Wlodzimierz Przewodowski, Bonin (PL)

(73) Assignee: Instytut Hodowli i Aklimatyzacji Roslin—Panstwowy Instytut Badawczy, Radzikow (PL)

( * ) Notice: Subject to any disclaimer, the term of this patent is extended or adjusted under 35 U.S.C. 154(b) by 621 days.

(21) Appl. No.: 12/676,671

(22) PCT Filed: Sep. 16, 2008

(86) PCT No.: PCT/PL2008/050015

§ 371 (c)(1),
(2), (4) Date: Jun. 17, 2010

(87) PCT Pub. No.: WO2009/035357

PCT Pub. Date: Mar. 19, 2009

(65) Prior Publication Data

US 2010/0255511 A1 Oct. 7, 2010

(30) Foreign Application Priority Data

Sep. 16, 2007 (PL) .......................................... 383361
Sep. 16, 2007 (PL) .......................................... 383362
Sep. 16, 2007 (PL) .......................................... 383363
Sep. 16, 2007 (PL) .......................................... 383364
Sep. 16, 2007 (PL) .......................................... 383365
Sep. 16, 2007 (PL) .......................................... 383366

(51) Int. Cl.
*G01N 33/53* (2006.01)

(52) U.S. Cl.
USPC .......... 435/7.1; 436/512; 436/547; 435/70.21

(58) Field of Classification Search
None
See application file for complete search history.

(56) References Cited

U.S. PATENT DOCUMENTS 6,015,681 A * 1/2000 Ralls et al. .................... 435/7.32
6,602,669 B2 * 8/2003 Letsinger et al. ............ 435/6.11
2002/0176084 A1 * 11/2002 Garini ........................... 356/445
2004/0089079 A1 * 5/2004 Engebretson .............. 73/863.23
2005/0244943 A1 * 11/2005 Ladisch et al. ............. 435/252.3
2006/0141546 A1 * 6/2006 Pugia et al. .................. 435/7.32
2009/0054254 A1 * 2/2009 Throsby et al. .................. 506/9

FOREIGN PATENT DOCUMENTS

DE 293606 A5 9/1991

OTHER PUBLICATIONS

Baer et al., Serological detection of nonmucoid strains of *Clavibacter michiganensis* subsp sepedonicus in potato, 1993, Phytopathology, 83(2):pp. 157-163.*

Karir et al., Surface modification of polystyrene using polyaniline nanostructures for biomolecule adhesion in radioimmunoassays, 2006, Anal Chem, 78(11): pp. 3577-3582.*

Slyvestre et al., A collagen-like surface glycoprotein is a structural component of the *Bacillus anthracis* exosporium, 2002, Molecular Microbiology, 45(1): pp. 169-178.*

Baer Debra et al., "Serological detection of nonmucoid strains of *Clavibacter michiganesis* ssp. Sepedonicus in potato", Phytopathology, vol. 83, No. 2, 1993, pp. 157-163.

De Boer S.H. et al., "Production of Monoclonal Antibodies to *Corynebacterium-Sepedonicum*", Phytopathology, vol. 74, No. 12, 1984, pp. 1431-1434.

De Boer S. H. et al., "An elisa Test for Bacerial ring Rot of Potato With a New Monoclonal Antibody", Plant Disease, vol. 72, No. 10, 1988, pp. 874-878.

De Leon L. et al., "Detection of *Clavibacter michiganensis* subsp. *Michiganensis* in tomato seeds using immunomagnetic separation", Journal of Microbiological Methods, Elsevier, Amsterdam, NL, vol. 67, No. 1, Oct. 2006, pp. 141-149.

De Leon L. et al., "Evaluation of the efficacy of immunomagnetic separation for the detection of *Clavibacter michiganesis* subsp. *Michiganensis* in tomato seeds", Journal of Applied Microbiology, Mar. 2008, vol. 104, No. 3, Mar. 2008, pp. 778-786.

McCoy E.C. et al., "Superficial Antigens of *Campylobacter-fetus* Characterizaton of an Anti Phagocytic Component", Infection and Immunity, vol. 11, No. 3, 1975, pp. 517-525.

Logan S.M. et al., "Molecular Identification of Surface Protein Antigens of *Campylobacter-jejuni*", Infection and Immunity, vol. 42, No. 2, 1983, pp. 675-682.

Yakrus M et al., "Serological Relationships Among Strains of Erwinia-Chrysnthemi", Phytopathology, vol. 69, No. 5, 1979, pp. 517-522.

International Search Report issued by the Internatinal Searching Authority (ISA/EP) on Jun. 3, 2009 in connection with International Application No. PCT/PL2008/050013.

* cited by examiner

*Primary Examiner* — N. C. Yang
(74) *Attorney, Agent, or Firm* — Gary J. Gershik; Cooper & Dunham LLP

(57) ABSTRACT

The use of a bacterial antigen obtained from bacterial cells in the production of antibodies for immunological assays for detecting bacterial cells.

18 Claims, No Drawings

IMMUNOLOGICAL TESTS FOR THE PRESENCE OF BACTERIA WHICH MAKE USE OF ANTIBODIES OBTAINED USING A SPECIFIC METHOD

This application is a §371 national stage of PCT International Application No. PCT/PL2008/05015, filed Sep. 16, 2008, and claims priority of Polish Patent Application Nos. P.383361, P.383362, P.383363, P.383364, P.383365 and P.383366, filed Sep. 16, 2007, the contents of all of which are hereby incorporated by reference into this application.

The subject of the present invention is the use of a bacterial surface antigen obtained from bacterial cells in the production of antibodies for the manufacture of immunological tests for detecting bacterial cells, particularly of *Clavibacter michiganensis* subsp. *sepedonicus*.

*Clavibacter michiganensis* subsp. *sepedonicus* (Spickermann et Kotthoff) Davis et al. (Cms), the cause of potato bacterial ring rot, is one of the foremost pathogens of the potato (Lee et al. 1997, OEPP/EPPO 2006). Synonymous names of the pathogen include: *Corynebacterium michiganensis* subsp. *sepedonicus* (Spieckermann et Kotthof) Carlson et Vidaver, *Corynebacterium michiganensis* pv. *sepedonicus* (Spieckermann et Kotthof) Dye et Kemp as well as *Corynebacterium sepedonicus* (Spieckermann et Kotthof) Skaptason et Burkholder (OEPP/EPPO, 2006).

*Clavibacter michiganensis* subsp. *sepedonicus* is a gram-positive, rod-shaped or coccal bacteria (OEPP/EPPO, 2006) which, along with the genus *Rathayibacter*, form the phytopathogenic group *Corynebacteria* with a common phylogenetic ancestry (Lee et al. 1997). The colonies of most cultured strains are mucoidal, though intermediate and non-mucus producing strains also occur (Bishop et al. 1988, Baer and Gudmestadt 1993).

Cms virulence factors know to date are:

a) Acidic bacterial mucoidal proteins of 1-10 MDa (Jahr et al. 1999) are also characteristic of other subspecies of *C. michiganensis*. These are composed of several (I-III) polysaccharide components of similar chemical composition differing in terms of agglomeration (Westra and Slack 1992). The occurrence of component type IV, composed mostly of mannose, is characteristic only of Cms bacteria (Denny 1995). Bacterial mucus, on one hand protects bacteria against moisture loss, and on the other hand impedes transpiration and causes wilting through the physical occlusion of vascular bundles (Jahr et al. 1999). The chemical composition of bacterial mucus as well as its presence or absence are significant factors in the diagnostics of Cms bacteria based on serological tests, in which mucus components are usually presented as antigens. Correct pathogen evaluation on the basis of bacterial mucus is dependent not only on genetic factors, but also on chemical variability and mucus volume produced by individual strains of Cms bacteria (Bishop and Slack 1987, Baer and Gudmestadt 1993).

b) The cellulase produced by most examined Cms strains (Baer and Gudmestad 1993) takes part in the degradation of vascular bundle tissues, leading to the delamination of the external layers of the tuber from its core (Jahr et al. 1999, Nissinen et al. 2001). Laine and co-workers (2000) showed that the cellulase is encoded by a gene in a native plasmid, pCS 1, of Cms bacteria (Laine et al. 2000).

c) The toxic glycoproteoid isolated from Strobela (1970), through its high affinity to wall fragments and host cell membranes, most likely leads to disruptions in the permeability of the latter (Romanenko et al. 1997).

To date, no successful method has been found of direct chemical or biological action against the pathogen. Surface disinfection of tubers does little, since the bacteria reside in vascular bundles, to which the disinfectant has no access.

One of the most effective methods of limiting or eliminating the causal agent of potato bacterial ring rot is its early detection. This is essential during production, processing and distribution of plant material. Thus effective detection methods should be appropriately sensitive and specific, as well as being simple, fast, reliable and repeatable (Waleron et al. 2003).

According to phyto-sanitary requirements, the effective diagnostics of the causal agent of potato bacterial ring rot require the use of at least two laboratory tests based on different biological processes, along with a pathogenicity test (OEPP/EPPO, 2006). Depending on the expression of symptoms of potato bacterial ring rot, appropriate protocols are chosen: physiological, biochemical, serological, molecular and others (EC Directive 2006/56).

Physiological and biochemical tests used in routine controls facilitate the phenotyping of Cms. According to the latest EC directive, these tests must be performed using bacterial isolates obtained through passaging on agar media with glucose. Morphological comparisons must be performed in cultures derived following growth on agar media with glucose in the presence of a known Cms control (EC Directive 2006/56).

In the case of plants with evident symptoms, bacterial isolation on semi-selective NCP-88 media is performed (De la Cruz et al. 1992) as well as MTNA (Jansing and Rudolph 1998), whereas routine cultures of pure Cms bacteria make us of growth media such as nutrient agar medium (NA), dextrose nutrient agar (NDA), yeast peptone glucose agar (YPGA) as well as a mineral medium with glucose and yeast extract (YGM) (De Boer and Copeman 1980, EC Directive 2006/56).

One of the main problems with the detection and identification of Cms bacteria is the slow growth rate of this pathogen. With direct inoculation onto universal medium, exogenous saprophytic bacteria characterised by notably higher growth rates overgrow the entire surface of the medium, often making it impossible to successfully isolate pure Cms strains (OEPP/EPPO, 2006). Pathogen isolation on semi-selective media containing antibiotics such as polymyxin sulphate B, nalidixylic acid and cycloheximide (NCP-88) as well as trimetoprim, and amphotercine B (MTNA), makes it possible to decrease the amount of other bacteria. The most effective isolations on semi-selective media can be obtained following inoculation of aubergine plants with pathogenic cell extracts. Aubergine constitutes a good environment for selectively culturing the causal agent of potato bacterial ring rot (OEPP/EPPO 2006).

The pathogenicity test on young aubergine plants inoculated with a three-day culture of the tested isolate is used as a final test of latent infection as well as for the evaluation of virulence of cultures identified as Cms. This test is characterised by a relatively low sensitivity ($10^6$ CFU/ml) as well as being time-intensive, ca. 40 days. To shorten this time, tobacco is also used as an indicator plant. This test, however, has the drawback of lower sensitivity ($10^8$-$10^9$ CFU/ml) (OEPP/EPPO 2006).

One of the long used methods of identifying Cms bacteria has been Gramm staining of smears from the vascular bundles and tubers (Glick et al. 1944, Slack 1987). However, unequivocal diagnoses with this method are difficult due to the occurrence of other gram+ bacteria such as *Clostridium* ssp, *Bacillus* ssp., as well as saprophytic bacteria of the genus *Corynebacterium* (Crowley and De Boer 1982).

Some laboratories have made use of the latex agglutination test, making it possible to detect $10^7$ cells in 1 ml (Slack et al. 1979). Reverse passive hemagglutination assays with ovine erythrocytes coated with anti-Cms antibodies from rabbit serum or chicken egg yolk make it possible to discover the presence of Cms within 90 minutes at concentrations of $6\times10^6$ per 1 ml (Kohm and Eggers-Schumacher 1995).

The serological detection of the causal organism of potato bacterial ring rot continues to cause many difficulties due to the morphological differentiation of the forms of the pathogen (Mills and Russell 2003). Commonly used serological tests are immunofluorescence, IF (Slack et al. 1979, De Boer and Copeman 1980), as well as immunoenzymeatic tests, ELISA (Enzyme Linked Immunoabsorbent Assay) (Drennan et al. 1993, De Boer et al. 1994, 2005). Although ELISA assays are disallowed by the EPPO as screening assays, they are much more popular in North America. Using monoclonal MAb 9A1 antibodies in an IF test ensures high specificity (De Boer and Wieczorek 1984) and detection of Cms bacteria in the range of $10^4$ cells per ml of potato tissue extract (Baer and Gudmestad 1993). Often, sensitivity is increased through the use of cheaper, but less specific polyclonal antibodies. However, this solution has the drawback often yielding false positive results due to cross-reactions with other bacteria (Crowley and De Boer 1982) as well as not detecting non-mucus forming strains of Cms bacteria (Baer and Gudmestad 1993). The main antigen detected are not Cms cells, but soluble exopolysaccharides whose amounts in relation to cell numbers may vary (Lewosz 1997). Both methods, IF and ELISA, make it possible to detect Cms bacteria in potato tubers and stalks, wherein the immunofluorescent method exhibits higher specificity in tubers, whereas ELISA detects the pathogen with greater specificity in stalks (De Boer et al. 1994).

Modern diagnostics make use of traditional, well established methods of detecting microorganisms which have many advantages. They are usually time-intensive and require specialised laboratory equipment. This precludes field testing, where an almost instantaneous result is needed, and the sample should be analyzed on-site (Ł oś and W ę grzyn, 2005). Since to-date the most effective method of preventing bacterial pathogen dispersion has been early detection, such conditions must be met in an increasing number of procedures. The need exists for fast, sensitive and direct methods of detection, both specific and inexpensive, and which would facilitate real time control during plant growth, production and storage, as well as food distribution (De Boer and Beumer 1999).

Thus, the problem rests in finding a method of quantifying *Clavibacter michiganensis* subsp. *sepedonicus* (Cms) with immunological methods using polyclonal anti-Cms antibodies.

Unexpectedly, this problem has been solved through the use of the method according to the present invention.

The first subject of the present invention is the use of a bacterial surface antigen obtained from mucoidal bacteria through washing the bacteria in a buffer selected from among glycine-HCl or glycine-NaOH to produce an immunological tests for detecting mucoidal and non-mucoidal bacteria. Preferentially, the glycine-HCl solution is used at a concentration of 0.001-1 M, preferentially 0.05-0.5 M, as well as at a pH of 1.5-3.5. preferentially 2-3. Equally preferentially the glycine-NaOH solution is used at a concentration of 0.001-1 M, preferentially in the range 0.05-0.5 M, pH 9.5-12. preferentially in the range 10-11. Preferentially, the antibody is tagged radioactively or colloidally, where the antibody is preferentially coated with gold.

The second subject of the present invention is a method of detecting the presence of bacteria in an analysed sample, characterised in that the analysed sample is suspended in a buffered solution, the resulting solution is put into contact with the tagged antibody specific against the surface antigen of the bacterium to be detected, whereafter the solution is filtered on a filter impermeable to the bacteria, wherein the presence of tagged bacteria on the filter is evidence of said bacteria in the analysed sample. Preferentially, the antibodies are tagged with colloidal gold. Equally preferentially, antibodies specific against mucoidal bacteria are obtained through immunization using the bacterial antigen obtained from mucoidal bacteria through washing bacterial cells in buffered solutions of glycine-HCl or glycine-NaOH. Preferentially, the antibacterial membranes are cellulose, polycarbonate or other membranes. Preferentially, the presence of Cms bacteria is detected, whereas the presence of antibodies tagged with colloidal gold is detected with the reduction of silver ions on colloidal gold. Equally preferentially the method, is characterised in that the filtration makes use of activated large-pore polycarbonate membranes, permeable to bacteria and modified with glutaryl aldehyde, containing immobilised anti-Cms antibodies. In another equally preferential embodiment of the present invention, the method is characterised in that the membranes facilitate the selective immuno-trapping of Cms bacteria, wherein antibodies specific against the bacteria are obtained through immunization using the bacterial antigen obtained by rinsing bacteria with a buffered solution selected from among glycine-HCl or glycine-NaOH. In the next preferential embodiment of the present invention, the method is characterised in that the presence of Cms bacteria is detected. In the next equally preferential embodiment of the present invention, the method is characterised in that the presence of bacteria other than Cms is detected, wherein the detection of the presence on the filter of these bacteria depends on the antibodies used. In the next equally preferential embodiment of the present invention a method is characterised in that the presence of bacteria immuno-trapped on the filter is ascertained using antibodies. Preferentially, a method according to the present invention is characterised in that antibodies tagged with colloidal gold are used. Equally preferentially, a method according to the present invention is characterised in that antibodies tagged with colloidal gold are detected using the reduction of silver ions on the colloidal gold. In the next equally preferential embodiment of the present invention, the method is characterised in that antibodies tagged with a fluorochrome are used. In the next equally preferential embodiment of the present invention, the method is characterised in that a fluorochrome such as carbocyanin Cy3 or any other is used. Equally preferentially, a method according to the present invention is characterised in that the presence of bacteria immuno-trapped on the filter is evaluated through culturing the cells. Equally preferentially, a method according to the present invention is characterised in that the culturing of the bacterial cells occurs after placing the immobilising filter on the surface of the medium containing nutrients for the immuno-trapped bacterial cells. In the next equally preferential embodiment of the present invention, the method is characterised in that the medium may be a selective, semi-selective or mineral medium. Equally preferentially, a method according to the present invention is characterised in that the activation of the membranes encompasses the following: coating of the membranes with an aniline polymer, and chemical modification of the polyanilin.

The third subject of the present invention is a kit for detecting the presence of bacteria in the analysed sample, characterised in that it contains plates possessing surfaces coated with activated aniline modified with glutaryl aldehyde with immuno-trapped antibodies specific against the selected bacterial antigen. Preferentially, the plates are in the form of Petri dishes or others, composed of material selected from among: polystrene, polyethylene, polycarbonate or glass. Preferentially, the antibodies specific against mucoidal bacteria are obtained via immunization using the bacterial antigen obtained from bacterial cells through rinsing bacteria with a buffered solution selected from among glycine-HCl or glycine-NaOH. Preferentially, the antibodies used are tagged, wherein preferentially the tag is selected from among: colloidal gold, enzyme, or fluorochrome. Preferentially, a kit according to the present invention additionally contains nutrients for the immuno-trapped bacterial cells. Preferentially, the nutrients are selected from among: selective media, semi-selective media and mineral media. The subject of the present invention is also the use of the kit according to the present invention in detecting or live isolation of selected bacteria.

The fourth subject of the present invention is a kit for detecting the presence of bacteria in the analysed sample, characterised in that it contains an essentially granular immunoabsorbent possessing a chemically activated surface with colloidal gold and immobilised antibodies specific against the selected bacterial antigen. Preferentially, immunoabsorbent is in the form of a polycarbonate or mineral carrier, preferentially glass microspheres. Preferentially, antibodies specific against mucoidal bacteria are produced via immunisation with the bacterial antigen obtained bacterial cells via rinsing bacteria with a buffered solution selected from among glycine-HCl or glycine-NaOH. Preferentially, the antibodies are additionally tagged with a marker, wherein, preferentially, the marker is selected from among: colloidal gold, enzyme, a fluorescent tag or a fluorochrome. Preferentially, a kit according to the present invention additionally contains nutrients for the immuno-trapped bacterial cells, which are preferentially selected from among: selective, semi-selective or mineral media. The subject of the present invention is also the use of a kit according to the present invention for detecting or live isolation of selected bacteria.

In light of the above, the subject of the present invention is also an immunological assay of the ELISA, IFAS or other commonly known sort, characterised in that the antigen from bacterial cells, preferentially mucoidal bacteria such as Cms, has been produced according to a method encompassing a stage of rinsing bacteria with buffered solutions: glycine-HCl or glycine-NaOH in order to obtain the antigen for producing the antibodies. Equally preferentially, the antibody used in the immunological assay is tagged radioactively or colloidally. In the next embodiment of the present invention the antibody is coated with colloidal gold. A method of tagging bacteria using membranes, being the second subject of the present invention, particularly of polycarbonate membranes, possessing excellent physicochemical properties, yields a white background, on which the tagged bacteria are very visible. The hue of the tagged bacterial cells does not fade, as is the case for some fluorochromes. Staining with a conjugate of colloidal gold and then silver staining of tagged bacterial cells makes it possible to preserve the image for several months. The test is a simple and quick method for evaluating the presence of Cms bacteria isolated from pure cultures in over a dozen samples simultaneously. Another advantage is the universal nature of the test, which, depending on the antibody used, can be used successfully against other bacteria. In the present invention, activation using an aniline polymer was used as a method of obtaining a functional immunobiochip. Test device surfaces subjected to chemical modification as well as immunoactivation according to the present invention, preferentially Petri dishes, may be produced from various materials (polystyrene, polyethylene, polycarbonate and glass). The present invention has made it possible to produce a functional substrate with novel chemical, optical and sorbent properties capable of activating antibodies (i.e. those directed against a new type of antigen, bacterial cells denuded of bacterial mucus to be used in the detection of Cms bacteria). The universality and functionality of this immunoabsorbent rests in the possibility of using it for every other bacteria, depending on the antibodies used. In the present invention, a facile immunoabsorbent was produced by using granular material a dextran gel (or glass microspheres), which were covalently coated with chitosan and colloidal gold following prior chemical modifications (via APTES, glutaryl aldehyde and aminocysteine). Of and in itself the dextran gel or glass microspheres are relatively inexpensive materials, easily obtained and functional. Both are in the form of microparticles, several to several dozen times larger than bacteria, and much heavier. This characteristic enables them to be used in binding and extracting bacteria and other biomolecules (viruses, proteins etc.) from a tested solution, without using additional equipment such as a centrifuge. Significant advantages gained in the present invention are: the possibility of binding various biomolecules on the surface of colloidal gold, which exhibits many advantageous characteristics as an absorbent medium, an increased absorptive surface of the medium, the possibility of covalently immobilizing antibodies and other biomolecules. A dextran hydrogel in the form of microspheres activated with antibodies against a given bacterium facilitates rapid contact between the antibodies and bacteria of interest. Unmodified dextran particles settle relatively slowly. After “weighing” with a layer of colloidal gold occluding on the surface of the dextran, they settle on the bottom within 2-3 minutes. Thus, additional procedures such as centrifugation are not necessary, to rinse and separate the microspheres from the impure solution.

EXAMPLE 1

The Use of Cms Cells Denuded of Mucus in the Production of Antibodies for Immune Assays Aqueous suspensions were made of the cells of the retained Cms bacterial strains, BPR-527, PD 221 as well as PD 406. The suspensions were washed thrice with dd$H_2O$ and centrifuged 15-25 min. at 7000 g on a Beckman J-21 centrifuge. The supernatant was discarded, an exopolysaccharides remaining on the bacterial cells were washed off 1-6 with 0.001-1M glycine-HCl buffer (pH 1.5-3.5), 1-6 times with 0.001-1M glicyne-NaOH buffer (pH 9.5-12), thrice with sterile $H_2O$, centrifuging the bacteria each time as above. Bacteria were lyophilised, and a mixture of the three lyophilisates was prepared in a ratio of 1:1:1 by mass. Subcutaneous immunisation was performed on a rabbit using a 1% aqueous solution of lyophilisate with Gerbu 100 adjuvant (1:1 v/v). The suspension was administered six times at biweekly intervals in 1 ml doses. Bleeding and antibody isolation was performed according to Ball et al. (1993). The blood was collected from the peripheral vein of the ear directly into centrifuge tubes. After collection, it was left to coagulate for 30 min. at 37° C., and then overnight at 4° C. The clot was gently separated from the walls and centrifuged for 15 minutes at 1000 g at 4° Cin a Beckman J-21 centrifuge. The serum was gently decanted, $NaN_3$ was added to a concentration of 0.02%, and then diluted tenfold with $ddH_2O$. An equal volume of saturated ammonium sulphate was added, gently mixed and left for 60 min. at RT in order to precipitate. The mixture was centrifuged for 5 min. at 8000 g on a Sorvall RC-5B centrifuge. The supernatant was discarded and the precipitate was dissolved in 0.5× PBS pH 7.4 in a volume double that of the initial serum volume, and dialysed overnight against three changes of the same buffer with 0.02% $NaN_3$. The dialysate was placed on a DEAE-cellulose column equilibrated with 0.5×PBS with 0.02% $NaN_3$. which was then used to wash the column, eluting the antibody. 3 ml fractions were collected whose $A_{280}$/$A_{250}$ absorbance ratio was =2.5÷2.7. The fractions were pooled and then passed through an antibacterial filter 0.2 μm and stored at 4° C. Antibody solutions were brought to a concentration of 2 mg/ml using the above mentioned buffer, accepting that IgG absorbance at 1 mg/ml at λ=280 nm is 1.4. Antibodies react with Cms cells encapsulated with mucus as well as slightly with cells partially denuded of bacterial mucus (Table 5).

ter 50 μl of each solution was collected and mixed with 50 μl of 2N NaCl. After determining optimal proportions, the colloidal gold was mixed with an appropriate amount of reduced antibodies and incubated for 5-60 minutes at RT with gentle mixing. To avoid non-specific absorption, the remaining colloidal gold surface was blocked with 1-20% BSA, whereas surplus unbound fragments were removed from the conjugate solution using 3-fold rinsing with TBS-BSA and concentration on an Eppendorf 5415C centrifuge (0.5-2 hours at 1000-4000 g). The precipitate from the last centrifugation was brought to an from OD535 nm=0.1-4.0 with the latter buffer and stored at 4° C. (IgG-Au1 solution).

EXAMPLE 3

A Method of Tagging Polyclonal Antibodies Against *Clavibacter Michiganensis* Subsp Random with Whole IgG Molecules Antibody solutions with concentrations of 0.01-1 mg/ml were made, which were dialysed overnight at 4° C. against 3

TABLE 5

A comparison of anti-Cms antibody titres against the moderately mucoidal strain Cms bacteria-PD 221 $10^4$ CFU/ml evaluated using an IF assay.

| | | Titre | | | | | | Blank (no IgG) |
|---|---|---|---|---|---|---|---|---|
| IgG | Suspension Cms bacteria | 1:200 | 1:400 | 1:800 | 1:1600 | 1:3200 | 1:6400 | — |
| IgG directed against bacterial mucus components | Bacteria in an aqueous suspension | + | + | +/− | −/+ | −/+ | −/+ | − |
| | Bacteria rinsed 3 times with $ddH_2O$ | + | + | +/− | −/+ | − | − | − |
| | Bacteria rinsed in acidic buffer | + | +/− | − | − | − | − | − |
| | Bacteria rinsed with basic buffer | + | +/− | + | − | − | − | − |
| IgG against bacterial cells without mucus | Bacteria in an aqueous suspension | − | − | − | − | − | − | − |
| | Bacteria rinsed 3 times with $ddH_2O$ | + | − | − | − | − | − | − |
| | Bacteria rinsed in acidic buffer | +/− | −/+ | − | − | − | − | − |
| | Bacteria rinsed with basic buffer | + | + | −/+ | − | − | − | − |

Legend:
+ - strong fluorescence,
+/− - moderate fluorescence,
−/+ - weak fluorescence,
− no fluorescence

EXAMPLE 2

A Method of Tagging Polyclonal Antibodies Against *Clavibacter Michiganensis* Subsp. *Sepedonicus*

In order to obtain Fab fragments, a reduction reaction was performed on the disulphide (S-S) bonds of whole IgG molecules, incubating them in EDTA-DTT in anoxic conditions. Six solutions with varying antibody concentrations were prepared, ranging from 20 do 500 μg/ml in 0.2 ml final volume of freshly prepared EDTA-DTT. The solutions, in 1.5 ml Eppendorf tubes, were incubated overnight at RT under 0.1 MPa vacuum. After opening, the solutions containing the IgG fragments were immediately combined with a standard colloidal gold solution from 4.0 at a 1:1 (v/v) ratio. The solutions were incubated for 10 minutes at RT with gentle mixing, whereafchanges of 10 mM borate buffer pH 9.2 and brought to a concentration of 0.1 mg/ml assuming that the A280 nm of such a solution is 0.140. Whereas a standard colloidal gold solution was brought to 10 mM with borate buffer pH 9.0. An initial titration was performed by making IgG solutions with concentrations ranging from 5 do 50 rig/ml, which were combined with a double volume of colloidal gold solution from 4.0, mixed and incubated 10 minutes at RT. Next, 50 μl of each solution was sampled and mixed with 50 μl 2N NaCl. After determining the optimal proportions, the colloidal gold was mixed with an appropriate amount of reduced antibodies and incubated 5-60 minutes at RT with gentle mixing. The procedure then followed that of Example 1. The precipitate obtained from the final centrifugation was brought, using TBS-BSA buffer, to an OD535 nm of 0.1-4.0 and stored 4° C. (IgG-Au2 solution).

EXAMPLE 5

Using Cms Cells Denuded of Mucus to Produce Antibodies for Immunological Assays

Aqueous suspensions were made of the cells of the retained Cms bacterial strains, BPR-527, PD 221 as well as PD 406. The suspensions were washed thrice with $ddH_2O$ and centrifuged 15-25 min. at 7000 g on a Beckman J-21 centrifuge. The supernatant was discarded, an exopolysaccharides remaining on the bacterial cells were washed off 1-6 with 0.001-1M glycine-HCl buffer (pH 1.5-3.5), 1-6 times with 0.001-1M glicyne-NaOH buffer (pH 9.5-12), thrice with sterile $H_2O$, centrifuging the bacteria each time as above. Bacteria were lyophilised, and a mixture of the three lyophilisates was prepared in a ratio of 1:1:1 by mass. Subcutaneous immunisation was performed on a rabbit using a 1% aqueous solution of lyophilisate with Gerbu 100 adjuvant (1:1 v/v). The suspension was administered six times at biweekly intervals in 1 ml doses. Bleeding and antibody isolation was performed according to Ball et al. (1993). The blood was collected from the peripheral vein of the ear directly into centrifuge tubes. After collection, it was left to coagulate for 30 min. at 37° C., and then overnight at 4° C. The clot was gently separated from the walls and centrifuged for 15 minutes at 1000 g at 4° Cin a Beckman J-21 centrifuge. The serum was gently decanted, $NaN_3$ was added to a concentration of 0.02%, and then diluted tenfold with $ddH_2O$. An equal volume of saturated ammonium sulphate was added, gently mixed and left for 60 min. at RT in order to precipitate. The mixture was centrifuged for 5 min. at 8000 g on a Sorvall RC-5B centrifuge. The supernatant was discarded and the precipitate was dissolved in 0.5× PBS pH 7.4 in a volume double that of the initial serum volume, and dialysed overnight against three changes of the same buffer with 0.02% $NaN_3$. The dialysate was placed on a DEAE-cellulose column equilibrated with 0.5×PBS with 0.02% $NaN_3$. which was then used to wash the column, eluting the antibody. 3 ml fractions were collected whose $A_{280}/A_{250}$ absorbance ratio was =2.5÷2.7. The fractions were pooled and then passed through an antibacterial filter 0.2 μm and stored at 4° C. Antibody solutions were brought to a concentration of 2 mg/ml using the above mentioned buffer, accepting that IgG absorbance at 1 mg/ml at $\lambda$=280 nm is 1.4. Antibodies react with Cms cells encapsulated with mucus as well as slightly with cells partially denuded of bacterial mucus (Table 1).

TABLE 1

A comparison of anti-Cms antibody titres against the moderately mucoidal strain Cms bacteria-PD 221 $10^4$ CFU/ml evaluated using an IF assay.

| IgG | Suspension of Cms bacteria | Titre 1:200 | 1:400 | 1:800 | 1:1600 | 1:3200 | 1:6400 | Blank (no IgG) — |
|---|---|---|---|---|---|---|---|---|
| IgG directed against bacterial mucus components | Bacteria in an aqueous suspension | + | + | +/− | −/+ | −/+ | −/+ | − |
| | Bacteria rinsed 3 times with $ddH_2O$ | + | + | +/− | −/+ | − | − | − |
| | Bacteria rinsed in acidic buffer | + | +/− | − | − | − | − | − |
| | Bacteria rinsed with basic buffer | + | +/− | + | − | − | − | − |
| IgG against bacterial cells without mucus | Bacteria in an aqueous suspension | − | − | − | − | − | − | − |
| | Bacteria rinsed 3 times with $ddH_2O$ | + | − | − | − | − | − | − |
| | Bacteria rinsed in acidic buffer | +/− | −/+ | − | − | − | − | − |
| | Bacteria rinsed with basic buffer | + | + | −/+ | − | − | − | − |

Legend:
+ - strong fluorescence,
+/− - moderate fluorescence,
−/+ - weak fluorescence,
− no fluorescence

EXAMPLE 6

Tagging of Polyclonal Antibodies Against *Clavibacter Michiganensis* Subsp. *Sepedonicus*

In order to obtain Fab fragments, a reduction reaction was performed on the disulphide (S-S) bonds of whole IgG molecules, incubating them in EDTA-DTT in anoxic conditions. Six solutions with varying antibody concentrations were prepared, ranging from 20 do 500 μg/ml in 0.2 ml final volume of freshly prepared EDTA-DTT. The solutions, in 1.5 ml Eppendorf tubes, were incubated overnight at RT under 0.1 MPa vacuum. After opening, the solutions containing the IgG fragments were immediately combined with a standard colloidal gold solution from 4.0 at a 1:1 (v/v) ratio. The solutions were incubated for 10 minutes at RT with gentle mixing, whereafter 50 μl of each solution was collected and mixed with 50 μl of 2N NaCl. After determining optimal proportions, the colloidal gold was mixed with an appropriate amount of reduced antibodies and incubated for 5-60 minutes at RT with gentle mixing. To avoid non-specific absorption, the remaining colloidal gold surface was blocked with 1-20% BSA, whereas surplus unbound fragments were removed from the conjugate solution using 3-fold rinsing with TBS-BSA and concentration on an Eppendorf 5415C centrifuge (0.5-2 hours at 1000-4000 g). The precipitate from the last centrifugation was brought to an from OD535 nm=0.1-4.0 with the latter buffer and stored at 4° C. (IgG-Au1 solution).

EXAMPLE 7

Tagging of Polyclonal Antibodies Against *Clavibacter Michiganensis* Subsp.

Antibody solutions with concentrations of 0.01-1 mg/ml were made, which were dialysed overnight at 4° C. against 3 changes of 10 mM borate buffer pH 9.2 and brought to a concentration of 0.1 mg/ml, assuming that the A280 nm of such a solution is 0.140. Whereas a standard colloidal gold solution was brought to 10 mM with borate buffer pH 9.0. An initial titration was performed by making IgG solutions with concentrations ranging from 5 do 50 μg/ml, which were combined with a double volume of colloidal gold solution from 4.0, mixed and incubated 10 minutes at RT. Next, 50 μl of each solution was sampled and mixed with 50 μl 2N NaCl. After determining the optimal proportions, the colloidal gold was mixed with an appropriate amount of reduced antibodies and incubated 5-60 minutes at RT with gentle mixing. The procedure then followed that of Example 1. The precipitate obtained from the final centrifugation was brought, using TBS-BSA buffer, to an OD535 nm of 0.1-4.0 and stored 4° C. (IgG-Au2 solution).

EXAMPLE 8

A Filtration Test for Detecting the Presence of *Ervinia Carotovora* Subsp. *Carotovora*

A series of suspensions of *Ervinia carotovora* subsp. *carotovora* were made in 10 mM PBS pH 7.2 in dilutions from 5*102 to 5*105 CFU/ml. 100 μl of each suspension was collected and 20 μl of the colloidal gold-tagged conjugate with anti-Ecc IgG were added to each. After 10 minutes, the mixture was filtered on polycarbonate membranes (porosity 0.4 μm) in a vacuum transfer apparatus. Following 1-6 rinses in 1×PBS pH 7.4 with 0.005-1% Tween 20, spot intensity on the membrane surface was examined or bacteria were observed under an optical microscope. To make the tagged Ecc bacteria more visible, the optical signal was amplified using reduction of silver ions on the colloidal gold. For this procedure, the membranes were placed into a freshly made solution of 0.015-0.5 M hydroquinone, 0.033-15 mM silver nitrate in 10 mM citrate buffer pH 2.5-4.0 and incubated around 2-12 min. The reaction was stopped by placing the membranes in $ddH_2O$ and drying on tissue paper. Ecc bacteria tagged with a conjugate of colloidal gold z with IgG-AP was contrasted enzymatically using BCIP/NBT as a substrate. Spots on the membrane were covered with 50 μl of freshly prepared BCIP/NBT solution and incubated 2-20 min. at room temperature. The reaction was stopped by placing the membranes in 1×PBS, pH 7.4 with 0.05% Tween 20 and drying on tissue paper. After amplifying the signal, the staining intensity of the spots on the membrane was examined using the unaided eye or bacteria were observed under an optical microscope.

EXAMPLE 9

A Filtration Test for Detecting the Presence of *Ervinia Amylovora*

A series of suspensions of *Ervinia amyloria* were made in 10 mM PBS pH 7.2 in dilutions from 5*102 to 5*105 CFU/ml. 100 μl of each suspension was collected and 20 μl of the colloidal gold-tagged conjugate with anti-Ea IgG were added to each.

After 10 minutes, the mixture was filtered on polycarbonate membranes (porosity 0.4 μm) in a vacuum transfer apparatus. Following 1-6 rinses in 1×PBS pH 7.4 with 0.005-1% Tween 20, spot intensity on the membrane surface was examined or bacteria were observed under an optical microscope.

To make the tagged Ea bacteria more visible, the optical signal was amplified using reduction of silver ions on the colloidal gold. For this procedure, the membranes were placed into a freshly made solution of 0.015-0.5 M hydroquinone, 0.033-15 mM silver nitrate in 10 mM citrate buffer pH 2.5-4.0 and incubated around 2-12 min. The reaction was stopped by placing the membranes in $ddH_2O$ and drying on tissue paper.

Ecc bacteria tagged with a conjugate of colloidal gold z with IgG-AP was contrasted enzymatically using BCIP/NBT as a substrate. Spots on the membrane were covered with 50 μl of freshly prepared BCIP/NBT solution and incubated 2-20 min. at room temperature. The reaction was stopped by placing the membranes in 1×PBS, pH 7.4 with 0.05% Tween 20 and drying on tissue paper.

After amplifying the signal, the staining intensity of the spots on the membrane was examined using the unaided eye or bacteria were observed under an optical microscope.

EXAMPLE 10

A Filtration Test for Detecting the Presence of Cms

A series of suspensions of *Clavibacter michiganensis* subsp. *michiganensis* were made in 10 mM PBS pH 7.2 in dilutions from 5*102 to 5*105 CFU/ml. 100 μl of each suspension was collected and 20 μl of the colloidal gold-tagged conjugate with anti-Cms IgG were added to each.

After 10 minutes, the mixture was filtered on polycarbonate membranes (porosity 0.4 μm) in a vacuum transfer apparatus. Following 1-6 rinses in 1×PBS pH 7.4 with 0.005-1% Tween 20, spot intensity on the membrane surface was examined or bacteria were observed under an optical microscope.

To make the tagged Ea bacteria more visible, the optical signal was amplified using reduction of silver ions on the colloidal gold. For this procedure, the membranes were placed into a freshly made solution of 0.015-0.5 M hydroquinone, 0.033-15 mM silver nitrate in 10 mM citrate buffer pH 2.5-4.0 and incubated around 2-12 min. The reaction was stopped by placing the membranes in $ddH_2O$ and drying on tissue paper.

EXAMPLE 12

Membrane Activation for Immuno Filtration Assays

The assay made use of polycarbonate membranes produced and chemically activated as in Example 1 and then activated with antibodies against Cms bacteria. IgG were immobilised covalently on the polyaniline surface using both a directed method and random method. In the first case, previously oxidated antibodies as well as chemically unmodified polyaniline were used, whereas in the second case chemically unmodified antibodies as well polyaniline activated with glutaryl aldehyde were used.

12.1 Directed Method

Polycarbonate membranes were activated as earlier in example 1, coated with 20 μl of a solution of oxidized antibodies at a concentration of 0.001-1 mg/ml in 1×PBS pH 7.4 with 20-60% glycerol. Membranes were incubated for 15-120 min. at 37° C. and washed thrice with 1×PBS pH 7.4. Next, 20 μl of 0.1-30% NaCNBH4 in 1×PBS pH 7.4 were placed on them for 15-120 min. under a fume extractor and washed thrice in 1×PBS pH 7.4. Activated surfaces were incubated 15-120 min. at 37° C. with blocking buffer (0.1-1.5% gelatine in 1×PBS, pH 7.4), and then washed thrice with 1×PBS pH 7.4 with 0.05% Tween 20.

12.2 Random Method

Polycarbonate membranes were activated with polyaniline and chemically modified with glutaryl aldehyde. Subsequently, 1-50 μl of antibody solutions with concentrations of 0.001-1 mg/ml in 1×PBS pH 7.4 and 20-60% glycerol, were immobilised. Next, the procedure was identical as in the directed method of antibody immobilisation.

EXAMPLE 13

Assay Using Bacteria

A suspension was prepared of Cms bacteria in a mixture of potato juice with 1×PBS pH 7.4 in dilutions ranging from 100 to 25000 CFU/ml. A membrane with immunoactivated spots of polyaniline laid out exactly like microwells in a vacuum blotter were placed between the covering layers of a vacuum blot. 1 ml of each solution was sampled and filtered gently through the membranes. Excess unbound bacteria were rinsed off thrice with 1×PBS pH 7.4 with 0.05% Tween 20, whereas immuno-trapped Cms bacteria were evaluated using various techniques:

- live bacteria were evaluated by placing the membrane with the active side down onto NCP-88 medium and incubating for 5-15 days at 15-30° C., or
- staining the bacteria with the immunofluorescent IFAS method, or
- staining the bacteria with a conjugate of colloidal gold with anti-Cms antibodies and then amplifying the signal with silver ions.

EXAMPLE 14

Determination of Cms Bacteria from Potato Tubers Stained with Colloidal Gold A mixture of potato tuber extract with 1×PBS pH 7.4 was prepared. The membrane with immunoactivated antibodies against *Clavibacter michiganensis* subsp. *sepedonicus* on spots of polyaniline laid out identically like microwells in a vacuum blotter, was placed between the halves of a vacuum blotter. 1 ml of each solution was sampled and filtered gently through the membranes. Excess unbound bacteria were rinsed off thrice with 1×PBS pH 7.4 with 0.05% Tween 20, whereas immuno-trapped Cms bacteria were evaluated by staining the bacteria with a conjugate of colloidal gold with anti-Cms antibodies and then amplifying the signal with silver ions.

EXAMPLE 15

Determination of Cms Bacteria from Potato Tubers Stained Using the IFAS Method A mixture of potato tuber extract with 1×PBS pH 7.4 was prepared. The membrane with immunoactivated antibodies against *Clavibacter michiganensis* subsp. *sepedonicus* on spots of polyaniline laid out identically like microwells in a vacuum blotter, was placed between the halves of a vacuum blotter. 1 ml of each solution was sampled and filtered gently through the membranes. Excess unbound bacteria were rinsed off thrice with 1×PBS pH 7.4 with 0.05% Tween 20, whereas immuno-trapped Cms bacteria were evaluated by staining using the immunofluorescent IFAS method and observing the results under a fluorescent microscope.

EXAMPLE 16

Immunization of Media Using the Immunofilter

A mixture of potato tuber extract with 1×PBS pH 7.4 was prepared. The membrane with immunoactivated antibodies against *Clavibacter michiganensis* subsp. *sepedonicus* on spots of polyaniline laid out identically like microwells in a vacuum blotter, was placed between the halves of a vacuum blotter. 1 ml of each solution was sampled and filtered gently through the membranes. Excess unbound bacteria were rinsed off thrice with 1×PBS pH 7.4 with 0.05% Tween 20, whereas immuno-trapped Cms bacteria were evaluated live, by placing the membrane activated side down directly onto NCP-88 medium and incubating for 10 days at 21° C. live, by placing the activated side of the membrane directly onto NCP-88 medium and incubating for 10 days at 21° C.

EXAMPLE 17

Preparation of Media

The assay made use of Petri dishes of polycarbonate or polystyrene or polyethylene or glass activated chemically as in application No. 07. and then antibodies against Cms bacteria were activated.

IgG was immobilised covalently on the surface of polyaniline in both a directed and random method. In the first case, use was made of antibodies previously oxidated as well as chemically unmodified polyaniline, whereas the in the second case chemically unmodified antibodies as well as polyaniline activated with glutaryl aldehyde are used.

Directed Method

Petri dishes activated with polyaniline as in Example 1 were coated with 20 μl of a solution of previously oxidized anti-Cms antibodies at a concentration of 0.001-10 mg/ml in 1×PBS pH 7.4 with 5-70% glycerol. The surface of the dishes was incubated for 15-120 min. at 37° C. and rinsed thrice with 1×PBS pH 7.4. Next, 20 μl of 0.1-30% $NaCNBH_4$ in 1×PBS pH 7.4. were loaded and placed for 15-120 min. under a fume extractor and subsequently rinsed thrice with 1×PBS pH 7.4. Activated surfaces were incubated for 15-120 min. at 37° C. in blocking buffer (0.1-1.5% gelatine in 1×PBS, pH 7.4), an then rinsed thrice in 1×PBS pH 7.4 with 0.05% Tween 20.

Random Method

Petri dishes activated with polyaniline and glutaryl aldehyde as in Example 1. 1-50 μl of anti-Cms antibody solution at a concentration of 0.001-1 mg/ml in 1×PBS pH 7.4 with 20-60% glycerol were immobilised. The Petri dishes were incubated for 15-120 min. at 37° C. and rinsed thrice in 1×PBS pH 7.4. Next, 20 μl was loaded of 0.1-30% $NaCNBH_4$ in 1×PBS pH 7.4, placed for 15-120 min. under a fume extractor rinsed thrice with 1×PBS pH 7.4. Activated surfaces were incubated for 15-120 min. at 37° C. in blocking buffer (0.1-1.5% gelatine or 1-15% bovine albumin in 1×PBS, pH 7.4), an then rinsed thrice in 1×PBS pH 7.4 with 0.05% Tween 20.

EXAMPLE 18

Assay Using Cms Bacteria

A suspension of Cms bacteria in buffered potato tuber extract (1×PBS pH 7.4 or another) in dilutions ranging from 100 to 25000 CFU/ml was prepared. The mixture was placed in a previously prepared immunoactive Petri dish with z polyaniline and incubated from 15 min. to 24 h at 4° C., RT or 37° C. Surplus unbound bacteria were rinsed off thrice with 1×PBS pH 7.4 with 0.05% Tween 20, whereas immuno-trapped Cms bacteria were evaluated with various methods:

a) observation following staining with:
   - a conjugate of colloidal gold with antibodies against the captured bacteria and a subsequent amplification of the signal through the reduction of silver on the colloidal gold, and subsequent observation under an optical microscope,
   - a conjugate of antibodies with an enzyme (i.e. alkaline phsophatase)
   - a conjugate of antibodies tagged with a fluorochrome (i.e. indocarbocyanin Cy3 or FITC) and observation under an epifluorescent microscope. In this case, not only the mechanical and chemical/absorbent properties of polyaniline are used, but equally its optical properties. This polymer is capable of quenching light exciting the fluorochrome, with which the bacteria re tagged. The resulting image is thus more highly contrasting. Normally, a dark substrate or an appropriate filter is used; or b) live evaluation through stripping the bacteria off using an appropriate alkaline buffer (i.e. 0.1 M of glycine-NaOH pH 10.5) and then subsequently immunization of the stripped cells onto a selective medium. Bacteria obtained in this way may be used in a biotest using indicator plants (bioindicators). This is extremely significant in ascertaining the virulence of a given bacterial strain, since it makes it possible to ascertain, whether and to what degree of virulence is in the isolated strain.

Said test may be realised in other variants:

EXAMPLE 19

Petri dishes modified chemically with polyaniline and glutaryl aldehyde as in Example 1 were coated with 25 μA of an antibody solution against bacteria *Clavibacter michiganensis* subsp. *sepedonicus*, with a concentration of 1 mg/ml in 1×PBS pH 7.4 z 20% glycerol. The Petri dishes were incubated for 30 min. at 37° C. and washed thrice in 1×PBS pH 7.4. Next, 25 μl 0.5% of $NaCNBH_4$ in 1×PBS pH 7.4 was added and they were placed for 10 min. under a fume extractor and were rinsed thrice in 1×PBS pH 7.4. Activated surfaces were incubated for 30 min. at 37° C. with a blocking buffer with 5% bovine albumin in 1×PBS, pH 7.4, whence they were rinsed thrice in 1×PBS pH 7.4 with 0.05% Tween 20.

The potato tuber extract was diluted 1:1 with 1×PBS pH 7.4. The mixture was placed in a prepared Petri dish with polyaniline coated with anti-Cms antibodies and incubated for 2 hours at 37° C. Excess unbound bacteria were removed by rinsing thrice with 1×PBS pH 7.4 with 0.05% Tween 20, whereas immuno-trapped Cms bacteria were stained using indirect immunofluorescence using a conjugate of goat anti-rabbit antibodies tagged with indocarbpcyanine Cy3. Stained bacterial cells were observed under a fluorescent microscope.

EXAMPLE 20

Petri dishes modified chemically with polyaniline and glutaryl aldehyde as in Example 1 were coated with 25 μA of an antibody solution against *Erwinia carotovora* subsp. *atroseptica*, with a concentration of 1 mg/ml in 1×PBS pH 7.4 z 20% glycerol. The Petri dishes were incubated for 30 min. at 37° C. and washed thrice in 1×PBS pH 7.4. Next, 25 μl 0.5% of $NaCNBH_4$ in 1×PBS pH 7.4 was added and they were placed for 10 min. under a fume extractor and were rinsed thrice in 1×PBS pH 7.4. Activated surfaces were incubated for 30 min. at 37° C. with a blocking buffer with 5% bovine albumin in 1×PBS, pH 7.4, whence they were rinsed thrice in 1×PBS pH 7.4 with 0.05% Tween 20.

The potato tuber extract was diluted 1:1 with 1×PBS pH 7.4. The mixture was placed in a prepared Petri dish with polyaniline coated with anti-Eca antibodies and incubated for 2 hours at 37° C. Excess unbound bacteria were removed by rinsing thrice with 1×PBS pH 7.4 with 0.05% Tween 20, whereas immuno-trapped Eca bacteria were stained using indirect immunofluorescence using a conjugate of goat anti-rabbit antibodies tagged with indocarbpcyanine Cy3. Stained bacterial cells were observed under a fluorescent microscope.

EXAMPLE 21

Petri dishes modified chemically with polyaniline and glutaryl aldehyde as in Example 1 were coated with 25 μl of an antibody solution against *Erwinia carotovora* subsp. *carotovora*, with a concentration of 1 mg/ml in 1×PBS pH 7.4 z 20% glycerol. The Petri dishes were incubated for 30 min. at 37° C. and washed thrice in 1×PBS pH 7.4. Next, 25 μl 0.5% of $NaCNBH_4$ in 1×PBS pH 7.4 was added and they were placed for 10 min. under a fume extractor and were rinsed thrice in 1×PBS pH 7.4. Activated surfaces were incubated for 30 min. at 37° C. with a blocking buffer with 5% bovine albumin in 1×PBS, pH 7.4, whence they were rinsed thrice in 1×PBS pH 7.4 with 0.05% Tween 20.

The potato tuber extract was diluted 1:1 with 1×PBS pH 7.4. The mixture was placed in a prepared Petri dish with polyaniline coated with anti-Ecc antibodies and incubated for 2 hours at 37° C. Excess unbound bacteria were removed by rinsing thrice with 1×PBS pH 7.4 with 0.05% Tween 20, whereas immuno-trapped Ecc bacteria were stained using indirect immunofluorescence using a conjugate of goat anti-rabbit antibodies tagged with indocarbocyanine Cy3. Stained bacterial cells were observed under an epifluorescent microscope.

This test is equally capable of performing a live evaluation, as well as an optical evaluation of the morphology of the identified cells.

EXAMPLE 22

Petri dishes modified chemically with polyaniline and glutaryl aldehyde as in Example 1 were coated with 25 μA of an antibody solution against bacteria *Clavibacter michiganensis* subsp. *sepedonicus*, with a concentration of 1 mg/ml in 1×PBS pH 7.4 z 20% glycerol. The Petri dishes were incubated for 30 min. at 37° C. and washed thrice in 1×PBS pH 7.4. Next, 25 μl 0.5% of $NaCNBH_4$ in 1×PBS pH 7.4 was added and they were placed for 10 min. under a fume extractor and were rinsed thrice in 1×PBS pH 7.4. Activated surfaces were incubated for 30 min. at 37° C. with a blocking buffer with 5% bovine albumin in 1×PBS, pH 7.4, whence they were rinsed thrice in 1×PBS pH 7.4 with 0.05% Tween 20.

The potato tuber extract was diluted 1:1 with 1×PBS pH 7.4. The mixture was placed in a prepared Petri dish with polyaniline coated with anti-Cms antibodies and incubated for 2 hours at 37° C. Excess unbound bacteria were removed by rinsing thrice with 1×PBS pH 7.4 with 0.05% Tween 20, whereas immuno-trapped Cms bacteria were stained using indirect immunofluorescence using a conjugate of goat anti-rabbit antibodies tagged with indocarbocyanine Cy3. Stained bacterial cells were observed under an epifluorescent microscope.

EXAMPLE 23

Petri dishes modified chemically with polyaniline and glutaryl aldehyde as in Example 1 were coated with 25 μA of an antibody solution against bacteria *Clavibacter michiganensis* subsp. *sepedonicus*, with a concentration of 1 mg/ml in 1×PBS pH 7.4 z 20% glycerol. The Petri dishes were incubated for 30 min. at 37° C. and washed thrice in 1×PBS pH 7.4. Next, 25 μl 0.5% of $NaCNBH_4$ in 1×PBS pH 7.4 was added and they were placed for 10 min. under a fume extractor and were rinsed thrice in 1×PBS pH 7.4. Activated surfaces were incubated for 30 min. at 37° C. with a blocking buffer with 5% bovine albumin in 1×PBS, pH 7.4, whence they were rinsed thrice in 1×PBS pH 7.4 with 0.05% Tween 20.

The potato tuber extract was diluted 1:1 with 1×PBS pH 7.4. The mixture was placed in a prepared Petri dish with polyaniline coated with anti-Cms antibodies and incubated for 2 hours at 37° C. Excess unbound bacteria were removed by rinsing thrice with 1×PBS pH 7.4 with 0.05% Tween 20, whereas immuno-trapped Cms bacteria were stained using a conjugate of colloidal gold with anti-Cms antibodies, and the optical signal obtained was amplified using the reduction of silver on the colloidal gold. Bacterial cells thus stained were observed under a optical microscope.

EXAMPLE 24

Petri dishes modified chemically with polyaniline and glutaryl aldehyde as in Example 1 were coated with 25 μA of an antibody solution against bacteria *Clavibacter michiganensis* subsp. *sepedonicus*, with a concentration of 1 mg/ml in 1×PBS pH 7.4 z 20% glycerol. The Petri dishes were incubated for 30 min. at 37° C. and washed thrice in 1×PBS pH 7.4. Next, 25 μl 0.5% of $NaCNBH_4$ in 1×PBS pH 7.4 was added and they were placed for 10 min. under a fume extractor and were rinsed thrice in 1×PBS pH 7.4. Activated surfaces were incubated for 30 min. at 37° C. with a blocking buffer with 5% bovine albumin in 1×PBS, pH 7.4, whence they were rinsed thrice in 1×PBS pH 7.4 with 0.05% Tween 20.

The potato tuber extract was diluted 1:1 with 1×PBS pH 7.4. The mixture was placed in a prepared Petri dish with polyaniline coated with anti-Cms antibodies and incubated for 2 hours at 37° C. Excess unbound bacteria were removed by rinsing thrice with 1×PBS pH 7.4 with 0.05% Tween 20, whereas immuno-trapped Cms bacteria were stained immunoenzymatically using a conjugate of anti-Cms antibodies with alkaline phosphatase and using NBT/BCIP as a substrate for the enzyme, yielding an insoluble product on the surface of Cms bacteria

EXAMPLE 25

Dextran or Glass Microspheres with Colloidal Gold

A portion of the purified microspheres were activated chemically at a temperature of 4-37° C. each time treating them for 15-60 min. with an triple volume of the appropriate modifying solution and rinsing five times with ten volumes of ddH2O after each step. The following were used 0.5-25% APTES in 96% ethanol, 0.06-25% aqueous glutaryl aldehyde, 0.001-1% chitosan in 0.01% acetic acid, 0.0001-1 M aqueous cystamine as well as a colloidal gold solution with an OD of 0.05-10.0. Glass microspheres were activated chemically, colloidal gold was settled, and antibodies were immobilised as above.

EXAMPLE 26

Detection of Bacteria Using Immunoadsorption on a Dextran Gel (or Glass Microspheres)

Dextran microspheres with colloidal gold were coated with anti-Cms IgG antibodies (0.0005-5 mg/ml) in 0.001-2M borate buffer pH 9.2 and incubated for 30 min. to 2 hours at a temperature in the range 4-37° C. After removing excess unbound antibodies, in order to block the remaining microsphere surface two volumes of 0.1-15% bovine albumin were added, rinsed thrice with 10 volumes of TBS-BSA pH 8.2 and placed in 4° C.

Extracts were made of potato tubers suspected of being infected with Cms bacteria and 1×PBS pH 7.4 was added at a ratio of 1:1. The following was placed into individual Eppendorf tubes: 2 ml of solution and 10-50 μA of immunoabsorbent (Dextran microspheres with colloidal gold coated with anti-Cms antibodies prepared as in Example 1). The whole mixture was incubated for 15 min. to 2 hours at room temperature with gentle mixing, to keep the microspheres in solution. After stopping the mixing and autologous sedimentation, the solution was removed from over the dextran grains and rinsed using 1×PBS pH 7.4 with 0.05% Tween 20, in this way removing surplus unbound bacteria. This was repeated twice, and then the bacteria trapped on the above immunoabsorbents were evaluated in two ways:

live evaluation by inoculating the microspheres onto a semi-selective medium, or immunoenzymatically, using a conjugate of anti-Cms IgG with alkaline phosphatase and incubating with a substrate solution of pNPP, performing absorbance readings at λ=405 nm following 1, 2 and 4 hours of incubation.

The test using glass microspheres is performed identically as for the dextran grains

TABLE 1

Detection of Cms bacteria using a live assay using glass microspheres and dextran grains. Results following 10 days of incubation of microspheres on a medium.

| Bacteria [CFU/ml] | Glass microspheres with colloidal gold Number of colonies/replicants | Dextran with colloidal gold Number of colonies/replicants |
|---|---|---|
| 0 | 0 (2 exogenous colonies)/2 | 0/2 |
| $5 * 10^1$ | 4/3 | 7/3 |
| $10^2$ | 10/3 | 18 (4 exogenous colonies)/3 |
| $5 * 10^2$ | 39 (3 exogenous colonies)/3 | 48 (2 exogenous colonies)/3 |
| $10^3$ | 87/3 | 165)/3 |

the sensitivity of detection in such a medium using immunoenzymatic protocol makes it possible to detect ca. 500 U/ml without any surplus equipment and time in the case of molecular methods. Below is a comparison of before and after modification of dextran grains and glass microspheres.

TABLE 2

Detection of Cms bacteria using an ELISA test using glass microspheres and dextran grains. Results following 1 hour of incubation pNPP as a substrate for AP. Values significantly differing from the background are in boldface.

| Bacteria | Glass microspheres standard modification | | Dextran grains standard modification | | Glass microspheres with colloidal gold | | Dextran grains with colloidal gold | |
|---|---|---|---|---|---|---|---|---|
| [CFU/ml] | E 405 | SD | E 405 | SD | E 405 | SD | E 405 | SD |
| 0 | 0.043 | 0.004 | 0.123 | 0.015 | 0.044 | 0.004 | 0.156 | 0.019 |
| $10^2$ | 0.028 | 0.003 | 0.012 | 0.001 | 0.024 | 0.002 | 0.102 | 0.012 |
| $5 * 10^2$ | 0.042 | 0.004 | 0.123 | 0.015 | **0.218** | 0.022 | **0.458** | 0.055 |
| $10^3$ | **0.111** | 0.011 | **0.225** | 0.027 | **0.604** | 0.060 | **0.658** | 0.079 |
| $10^4$ | **0.166** | 0.017 | **0.492** | 0.059 | **0.835** | 0.083 | **0.973** | 0.117 |
| $10^5$ | **0.215** | 0.021 | **0.702** | 0.084 | **0.865** | 0.086 | **1.302** | 0.156 |

Other embodiments of the test predict its use against other types of bacteria.

EXAMPLE 27

Dextran microspheres with colloidal gold were coated with anti-Cms IgG antibodies 0.5 mg/ml in 0.01 borate buffer pH 9.2 and incubated for 30 min. at a temperature in the range of 4-37° C. After removing excess unbound antibodies, in order to block the remaining microsphere surface two volumes of 10% bovine albumin were added, rinsed thrice with 10 volumes of TBS-BSA pH 8.2 and placed in 4° C.

Extracts were made of potato tubers suspected of being infected with Cms bacteria and 1×PBS pH 7.4 was added at a ratio of 1:1. The following was placed into individual Eppendorf tubes: 2 ml of solution and 30 μA of immunoabsorbent Dextran microspheres with colloidal gold coated with anti-Cms antibodies. The whole mixture was incubated for 30 min. at room temperature with gentle mixing, to keep the microspheres in solution. After stopping the mixing and autologous sedimentation, the solution was removed from over the dextran grains and rinsed using 1×PBS pH 7.4 with 0.05% Tween 20, in this way removing surplus unbound bacteria. This was repeated twice, and then the bacteria trapped on the above immunoabsorbents were evaluated immunoenzymatically using as a marker a conjugate of IgG anti-Cms with alkaline phosphatase and incubating with a substrate solution of pNPP, performing absorbance readings at λ=405 nm following 1, 2 and 4 hours of incubation.

EXAMPLE 28

Dextran microspheres with colloidal gold were coated with anti-*Erwinia carotovora* subsp. *carotovora* IgG antibodies 0.5 mg/ml in 0.01 borate buffer pH 9.2 and incubated for 30 min. at a temperature in the range of 4-37° C. After removing excess unbound antibodies, in order to block the remaining microsphere surface two volumes of 10% bovine albumin were added, rinsed thrice with 10 volumes of TBS-BSA pH 8.2 and placed in 4° C.

Extracts were made of potato tubers suspected of being infected with Ecc bacteria and 1×PBS pH 7.4 was added at a ratio of 1:1. The following was placed into individual Eppendorf tubes: 2 ml of solution and 30 μA of immunoabsorbent Dextran microspheres with colloidal gold coated with anti-Ecc antibodies. The whole mixture was incubated for 30 min. at room temperature with gentle mixing, to keep the microspheres in solution. After stopping the mixing and autologous sedimentation, the solution was removed from over the dextran grains and rinsed using 1×PBS pH 7.4 with 0.05% Tween 20, in this way removing surplus unbound bacteria. This was repeated twice, and then the bacteria trapped on the above immunoabsorbents were evaluated immunoenzymatically using as a marker a conjugate of IgG anti-Ecc with alkaline phosphatase and incubating with a substrate solution of pNPP, performing absorbance readings at λ=405 nm following 1, 2 and 4 hours of incubation.

The invention claimed is:

1. A method of detecting a specific bacteria in a sample, comprising the steps:

i) suspending the sample in a buffered solution;

ii) contacting the sample with an antibody specific against a surface antigen of the bacteria to be detected, wherein the antibody was raised against a bacterial cell which has been denuded of bacterial mucus via washing the bacterial cell with water, then with a buffered solution of glycine-HCl, then with a buffered solution of glycine-Na OH, and then with water;

iii) filtering the solution through a membrane: and iv) detecting a presence of bacteria tagged via the antibody on the membrane, wherein the presence of bacteria tagged via the antibody on the membrane is evidence of the bacteria in the sample.

2. The method according to claim 1, wherein the antibody is tagged with colloidal gold.

3. The method according to claim 1, wherein the membrane of step iii) is low porosity and impermeable to bacteria.

4. The method according to claim 1, wherein the membrane of step iii) is high porosity and permeable to bacteria.

5. The method according to claim 1, wherein the bacteria is subspecies *Clavibacter michiganensis* subsp. *sepedonicus*.

6. The method according to claim 1, wherein the bacteria is other than subspecies *Clavibacter michiganensis* subsp. *sepedonicus*.

7. The method according to claim 1, wherein the presence of bacteria tagged via the antibody on the membrane is detected by using antibodies in conjugation with an enzymatic contrasting agent.

8. The method according to claim 2, wherein the presence of bacteria tagged via the antibody on the membrane is detected by using the reduction of silver ions on the colloidal gold.

9. The method according to claim 1, wherein the membrane of step iii) is an activated polycarbonate membrane modified with glutaryl aldehyde and containing immobilized antibodies.

10. The method according to claim 9, wherein the immobilized antibodies are specific against a surface antigen of bacteria of the subspecies *Clavibacter michiganensis* subsp. *sepedonicus*.

11. The method according to claim 9, wherein the presence of bacteria tagged via the antibody on the membrane is determined using antibodies in conjugation with an enzymatic contrasting agent.

12. The method according to claim 9, wherein the presence of bacteria tagged via the antibody on the membrane is determined using antibodies tagged with colloidal gold.

13. The method according to claim 12, wherein the antibodies tagged with colloidal gold are detected using the reduction of silver ions on the colloidal geld.

14. The method according to claim 9, wherein the presence of bacteria tagged via the antibody on the membrane is determined using antibodies tagged with a fluorochrome.

15. The method according to claim 14, wherein the fluorochrome is carbocyanine Cy3.

16. The method according to claim 1, further comprising step v) after step iv), said step v) comprising culturing bacterial cells on the membrane by placing the membrane on the surface of a medium containing nutrients for bacterial cells.

17. The method according to claim 9, wherein the activated polycarbonate membrane is prepared by coating a membrane with a polymer of aniline, chemical modification of the polymer of aniline with glutaryl aldehyde, coating with antibodies, blocking and rinsing with a buffer.

18. The method according to claim 1, wherein the antibody is tagged with colloidal gold, the presence of bacteria tagged via the antibody on the membrane is detected by using the reduction of silver ions on the colloidal gold, and the bacteria is subspecies *Clavibacter michiganensis* subsp. *sepedonicus*.

* * * * *

UNITED STATES PATENT AND TRADEMARK OFFICE

CERTIFICATE OF CORRECTION

PATENT NO. : 8,642,275 B2
APPLICATION NO. : 12/676671
DATED : February 4, 2014
INVENTOR(S) : Wlodzimierz Przewodowski It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 714 days.

Signed and Sealed this
Twenty-ninth Day of September, 2015

Michelle K. Lee
*Director of the United States Patent and Trademark Office*